(12) United States Patent
Fujita

(10) Patent No.: US 9,284,614 B2
(45) Date of Patent: Mar. 15, 2016

(54) PRE-TREATMENT METHOD FOR PLANT BIOMASS HYDROLYSIS REACTION RAW MATERIALS AND PLANT BIOMASS SACCHARIFICATION METHOD

(75) Inventor: Ichiro Fujita, Minato-ku (JP)

(73) Assignee: SHOWA DENKO K.K., Tokyo (JP)

( * ) Notice: Subject to any disclaimer, the term of this patent is extended or adjusted under 35 U.S.C. 154(b) by 230 days.

(21) Appl. No.: 14/006,482

(22) PCT Filed: Mar. 8, 2012

(86) PCT No.: PCT/JP2012/055946
§ 371 (c)(1),
(2), (4) Date: Sep. 20, 2013

(87) PCT Pub. No.: WO2012/128055
PCT Pub. Date: Sep. 27, 2012

(65) Prior Publication Data
US 2014/0007862 A1    Jan. 9, 2014

(30) Foreign Application Priority Data

Mar. 22, 2011 (JP) .................................. 2011-062681

(51) Int. Cl.
*C13K 1/02* (2006.01)
*B09B 3/00* (2006.01)
*C12P 19/02* (2006.01)

(52) U.S. Cl.
CPC ... *C13K 1/02* (2013.01); *B09B 3/00* (2013.01); *C12P 19/02* (2013.01); *C12P 2201/00* (2013.01)

(58) Field of Classification Search
None
See application file for complete search history.

(56) References Cited

U.S. PATENT DOCUMENTS

| 5,204,310 | A * | 4/1993 | Tolles et al. ................... 502/416 |
| 8,524,959 | B1 * | 9/2013 | O'Connor et al. ............ 585/240 |
| 2009/0308787 | A1 | 12/2009 | O'Conner et al. | |
| 2010/0167368 | A1 | 7/2010 | Kawasaki | |

FOREIGN PATENT DOCUMENTS

| CN | 101691617 A | 4/2010 |
| JP | 2006-129735 A | 5/2006 |
| JP | 2008-271787 A | 11/2008 |
| JP | 2008-297229 A | 12/2008 |
| JP | 2009-201405 A | 9/2009 |
| JP | 2009-536235 A | 10/2009 |
| JP | 2010-98994 A | 5/2010 |
| WO | 2007/128798 A1 | 11/2007 |
| WO | 2008/132605 A1 | 11/2008 |
| WO | 2009/004951 A1 | 1/2009 |
| WO | 2010/068748 A1 | 6/2010 |

OTHER PUBLICATIONS

Machine translation of JP 2006-129735 Yukihiko Matsumura Publ May 25, 2006.*
Translation of International Preliminary Report of Patentability for Application No. PCT/JP2012/055946, mailed Oct. 11, 2013.
European Search Report dated Aug. 6, 2014 issued in application No. 12760365.2-1358.
International Search Report for PCT/JP2012/055946 dated Apr. 24, 2012.

* cited by examiner

*Primary Examiner* — Melvin C Mayes
*Assistant Examiner* — Douglas Call
(74) *Attorney, Agent, or Firm* — Sughrue Mion, PLLC

(57) ABSTRACT

The invention relates to: a pre-treatment method for plant biomass hydrolysis reaction raw materials characterized in comprising a process for mixing a solid catalyst and solid substrate beforehand and grinding same simultaneously (grinding process); a plant biomass hydrolysis reaction raw material pre-treated by said pre-treatment method; and a plant biomass saccharification method comprising a process for hydrolyzing said hydrolysis reaction raw material. The invention provides an efficient and practical pre-treatment method for plant biomass hydrolysis reaction raw materials that can improve the saccharification yield and saccharide concentration of plant biomass hydrolysis reactions, a plant biomass hydrolysis reaction raw material obtained therefrom, and a plant biomass saccharification method.

7 Claims, 4 Drawing Sheets

PRE-TREATMENT METHOD FOR PLANT BIOMASS HYDROLYSIS REACTION RAW MATERIALS AND PLANT BIOMASS SACCHARIFICATION METHOD

CROSS REFERENCE TO RELATED APPLICATIONS

This application is a National Stage of International Application No. PCT/JP2012/055946, filed on Mar. 8, 2012, which claims priority from Japanese Patent Application No. 2011-062681, filed on Mar. 22, 2011, the contents of all of which are incorporated herein by reference in their entirety.

TECHNICAL FIELD

The present invention relates to a pre-treatment method of a raw material for a plant biomass hydrolysis reaction and a saccharification method for a plant biomass. More specifically, the present invention relates to a pre-treatment method of a raw material for a plant biomass hydrolysis reaction that can improve a saccharification yield and a sugar concentration in a hydrolysis reaction of a plant biomass including cellulose and hemicellulose with a solid catalyst, and a saccharification method for a plant biomass.

BACKGROUND ART

In recent years, many studies have been made on use of useful substances converted from recyclable biomass resources produced from plants and the like. Cellulose contained in a plant biomass as a major component is characterized by being insoluble in water or a usual solvent and being persistent because it is a polymer formed of β-1,4-linked glucose units, forms hydrogen bonds within and between molecules, and thus exhibits high crystallinity. In recent years, a study on a reaction using a solid catalyst that is recyclable and can reduce an environmental burden has been made as a cellulose hydrolysis method which substitutes for a sulfuric acid method or an enzyme method.

The hydrolysis reaction of cellulose with a solid catalyst is a solid-solid reaction, and a rate of the reaction is limited by contact property of the catalyst and a substrate. Therefore, in order to realize a highly-efficient reaction, it is necessary to develop a highly active catalyst as well as a treatment method of improving reactivity. For example, as a method of improving reactivity in a solid-solid reaction system, there are given a method involving mixing and preheating a pulverized substrate, a catalyst and preheating steam (JP-A-2008-297229, Patent Document 1) and a method involving allowing a catalyst and a substrate to react under irradiation with microwaves (JP-A-2010-98994, Patent Document 2).

However, Patent Document 1 discloses that about 70% of cellulose is degraded, but does not specifically describe the yield of a sugar obtained as a degraded product, and the effect is unknown. In addition, in Patent Document 2, the glucose yield is about 30%, and a high reaction yield has not been achieved. Further, it is necessary to introduce an expensive microwave irradiation apparatus, and the method is problematic in practicality.

In addition, as a method of improving reactivity in a pseudo-liquid-solid reaction system, there is given a method involving adding cellulose to a cluster acid catalyst in a pseudo-molten state to perform hydrolysis (JP-A-2008-271787, Patent Document 3). However, the method of Patent Document 3 is problematic in practicality due to difficulty in controlling water content during a reaction, requirement of many steps for separation of the catalyst from the product, and use of an organic solvent.

For the above-mentioned reasons, it has been desired to establish a pre-treatment method for a hydrolysis reaction raw material that can achieve a high sugar yield without introduction of an expensive apparatus and addition of a further component in a hydrolysis reaction of a plant biomass with a solid catalyst.

CITATION LIST

Patent Document

[Patent Document 1] JP-A-2008-297229
[Patent Document 2] JP-A-2010-98994
[Patent Document 3] JP-A-2008-271787 (WO 2008/132605 A1)

SUMMARY OF INVENTION

Technical Problem

An object of the present invention is to provide an efficient and practical pre-treatment method for a plant biomass hydrolysis reaction raw material that can improve a saccharification yield and a sugar concentration in a hydrolysis reaction of a plant biomass without introduction of an expensive apparatus and addition of a further component, a plant biomass hydrolysis reaction raw material obtained therefrom, and a saccharification method for a plant biomass.

Solution to Problem

The inventor of the present invention made extensive studies to solve the above-mentioned problems. As a result, the inventor has found that, in a hydrolysis reaction of a plant biomass with a solid catalyst, the reaction yield and concentration of a sugar containing a monosaccharide such as glucose as a major component in a reaction solution can be improved by preliminarily mixing and simultaneously pulverizing the catalyst and a substrate (plant biomass) and hydrolyzing the resultant material, thus completing the present invention.

That is, the present invention includes a pre-treatment method for a plant biomass hydrolysis reaction raw material according to the following [1] to [9], a plant biomass hydrolysis reaction raw material according to the following [10], and a saccharification method for a plant biomass according to the following [11].

[1] A pre-treatment method for a plant biomass hydrolysis reaction raw material, comprising pulverization step that comprises preliminarily mixing and simultaneously pulverizing a solid catalyst and a solid substrate.

[2] The pre-treatment method for a plant biomass hydrolysis reaction raw material according to the above-mentioned [1], in which the solid catalyst is a carbon material.

[3] The pre-treatment method for a plant biomass hydrolysis reaction raw material according to the above-mentioned [1] or [2], in which the carbon material is alkali-activated carbon, steam-activated carbon, or mesoporous carbon.

[4] The pre-treatment method for a plant biomass hydrolysis reaction raw material according to any one of the above-mentioned [1] to [3], in which the solid substrate is a polysaccharide derived from a plant biomass.

[5] The pre-treatment method for a plant biomass hydrolysis reaction raw material according to any one of the above-mentioned [1] to [4], in which the pulverization step is carried out using a tumbling ball mill, a vibrating ball mill, a mixing mill, or a planetary ball mill.

[6] The pre-treatment method for a plant biomass hydrolysis reaction raw material according to any one of the above-mentioned [1] to [5], in which a median diameter of a mixture of the solid catalyst and the solid substrate as the reaction raw material after the pulverization step is 1 to 100 µm.

[7] The pre-treatment method for a plant biomass hydrolysis reaction raw material according to the above-mentioned [6], in which the median diameter is 1 to 30 µm.

[8] The pre-treatment method for a plant biomass hydrolysis reaction raw material according to any one of the above-mentioned [1] to [7], in which a mass ratio between the solid catalyst and the solid substrate is 1:100 to 10:1.

[9] The pre-treatment method for a plant biomass hydrolysis reaction raw material according to the above-mentioned [8], in which a mass ratio between the solid catalyst and the solid substrate is 1:10 to 1:1.

[10] A plant biomass hydrolysis reaction raw material, which is treated by the pre-treatment method according to any one of the above-mentioned [1] to [9].

[11] A saccharification method for a plant biomass, comprising the step of hydrolyzing the hydrolysis reaction raw material according to the above-mentioned [10].

Advantageous Effects of Invention

When a plant biomass treated by the pre-treatment method for a hydrolysis reaction raw material of the present invention, which includes the step of preliminarily mixing and simultaneously pulverizing a solid catalyst and a solid substrate, is hydrolyzed, a reaction solution containing a sugar product containing a monosaccharide such as glucose as a major component can be obtained at a high yield. Further, when the concentration of the hydrolysis reaction raw material is raised by the pre-treatment method of the present invention, a reaction solution in which the sugar product is accumulated at a high concentration can be obtained.

DESCRIPTION OF EMBODIMENTS

Figure 1:
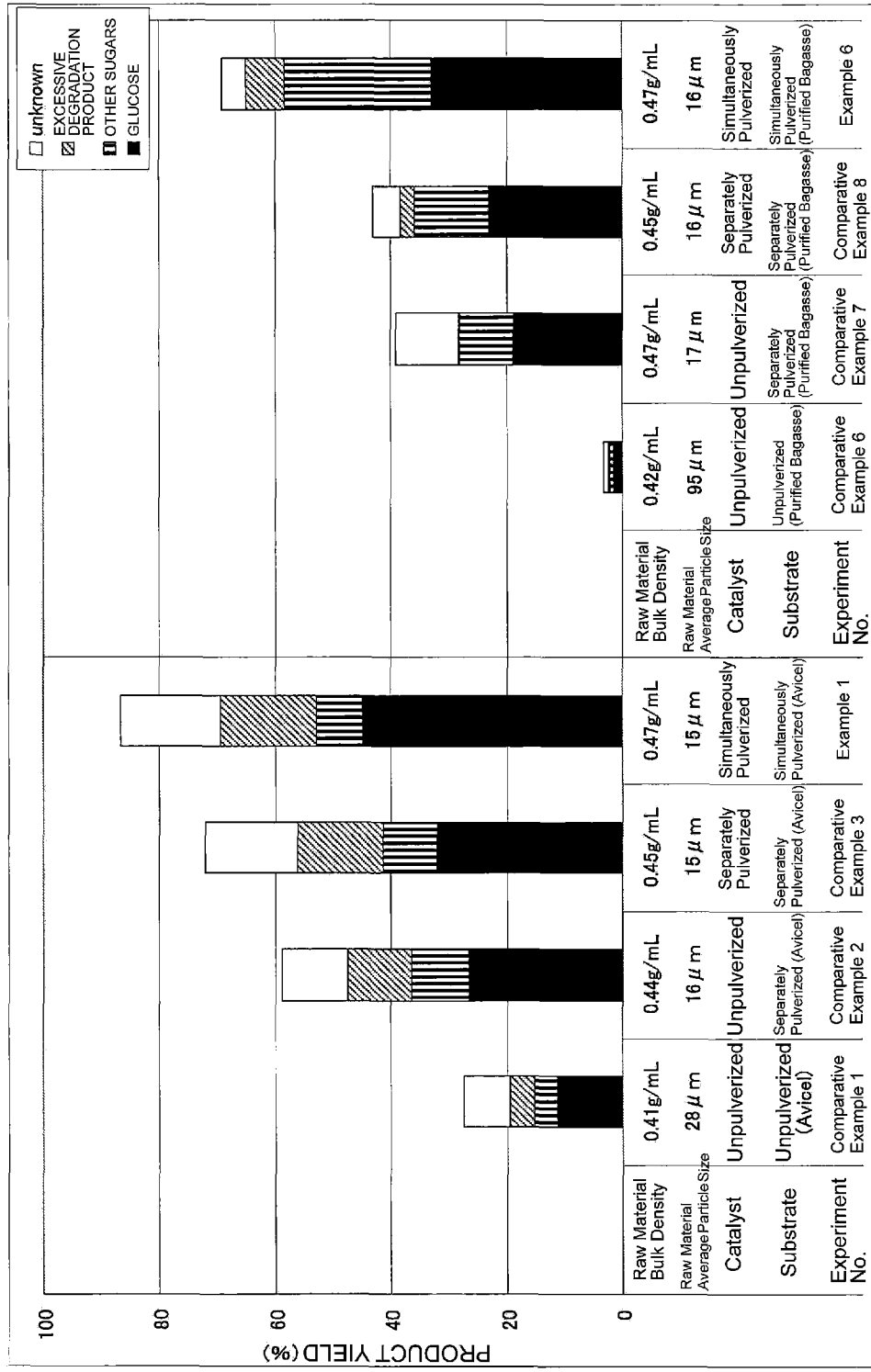
FIG. 1 is a graph showing a comparison of reaction product yields under different pulverization conditions (not pulverized, separately pulverized and mixed, or simultaneously pulverized) of a substrate (Avicel or purified bagasse) and a catalyst as reaction raw materials. In the figure, the black part represents a yield of glucose, the vertical stripe part represents a yield of a sugar other than glucose, the shaded part represents a yield of an excessive degradation product, and the white part represents a yield of an unknown substance.

Hereinafter, the present invention is described in detail.

A pre-treatment method for a plant biomass hydrolysis reaction raw material of the present invention is characterized by the presence of a step of preliminarily mixing and simultaneously pulverizing a solid catalyst and a solid substrate.

[Solid Substrate (Plant Biomass)]

In the present invention, the "plant biomass" is, for example, a biomass such as rice straw, straw, sugarcane straw, chaff, bagasse, a broadleaf tree, bamboo, a coniferous tree, kenaf, furniture waste, construction waste, waste paper or a food residue, which mainly contains cellulose or hemicellulose. It should be noted that the term "biomass" generally refers to "recyclable organic resource of biologic origin, excluding fossil resources."

In the present invention, the term "polysaccharide derived from a plant biomass" refers to a residue obtained by subjecting the plant biomass to a treatment such as alkali steam treatment, alkaline sulfite steam treatment, neutral sulfite steam treatment, alkaline sodium sulfide steam treatment, or ammonia steam treatment, and then to a delignification treatment by solid-liquid separation and water washing. In addition, it may be one containing two or more polysaccharides out of cellulose, hemicellulose and lignin, and may be industrially prepared cellulose, xylan, cellooligosaccharide or xylooligosaccharide. Further, it may contain an ash content such as silicon, aluminum, calcium, magnesium, potassium or sodium, which is derived from a plant biomass, as an impurity.

The polysaccharide derived from a plant biomass may be in a dry form or a wet form, and may be crystalline or non-crystalline. The particle size of the polysaccharide derived from a plant biomass is not particularly limited as long as the polysaccharide can be subjected to the pulverization treatment. From the viewpoint of pulverization efficiency, the particle size is preferably 20 µm or more and several thousand µm or less.

[Solid Catalyst]

The solid catalyst used in the present invention is not particularly limited as long as the catalyst can hydrolyze a polysaccharide in a plant biomass. For example, the catalyst preferably has an activity to hydrolyze a glycoside bond typified by β-1,4 glycosidic bonds between glucose units that form cellulose contained as a major component.

As the solid catalyst, for example, one kind of carbon materials and transition metals may be used alone, or two or more kinds thereof may be used in combination.

As the carbon material, for example, one kind of activated carbon, carbon black and graphite may be used alone, or two or more kinds thereof may be used in combination. From the viewpoint of improving reactivity by increasing an area for contact with a substrate, the carbon material is preferably porous and/or particulate. From the viewpoint of promoting hydrolysis by expressing an acid center, the carbon material preferably has a surface functional group such as a phenolic hydroxyl group, a carboxyl group, a sulfonyl group or a phosphate group. As a porous carbon material having a surface functional group, activated carbon may be used, which is prepared by a physical method involving treating a wood material such as coconut husk, bamboo, pine, walnut husk, or bagasse; or coke, phenol and the like at high temperature with a gas such as steam, carbon dioxide or air, or by a chemical method involving treating them at high temperature with a chemical reagent such as an alkali or zinc chloride.

The transition metal is, for example, at least one kind selected from the group consisting of ruthenium, platinum, rhodium, palladium, iridium, nickel, cobalt, iron, copper, silver and gold. One kind of those transition metals may be used alone, or two or more kinds thereof may be used in combination. One selected from platinum group metals including ruthenium, platinum, rhodium, palladium and iridium is preferred from the viewpoint of having a high catalytic activity, and one selected from ruthenium, platinum, palladium, and rhodium is particularly preferred from the viewpoints of having a high rate of conversion of cellulose and selectivity of glucose.

[Simultaneous Pulverization Treatment for Catalyst and Substrate]

As mentioned above, the present invention is characterized by use of a product obtained by preliminarily mixing and simultaneously pulverizing a solid catalyst and a solid substrate as a hydrolysis reaction raw material. The pulverization means is not particularly limited as long as the means has a function to homogeneously and finely pulverize the substrate and catalyst. For example, the mode of the apparatus may be a dry mode or a wet mode. In addition, the pulverization system of the apparatus may be a batch system or a continuous system. Further, the pulverization force of the apparatus may be any of impact, compression, shearing, friction, and the like.

Specific examples of the apparatus that may be used in the pulverization treatment include: tumbling ball mills such as a pot mill, a tube mill and a conical mill; vibrating ball mills such as a circular vibration type vibration mill, a rotary vibration mill and a centrifugal mill; mixing mills such as a media agitating mill, an annular mill, a circulation type mill and a tower mill; jet mills such as a spiral flow jet mill, an impact type jet mill, a fluidized bed type jet mill and a wet type jet mill; shear mills such as a Raikai mixer and an angmill; colloid mills such as a mortar and a stone mill; impact mills such as a hammer mill, a cage mill, a pin mill, a disintegrator, a screen mill, a turbo mill, and a centrifugal classification mill; and a planetary ball mill as a mill of a type that employs rotation and revolution movements.

In the cellulose hydrolysis treatment, a pre-treatment for amorphization by pulverization of the substrate is carried out to improve reactivity. The simultaneous pulverization treatment of the present invention can also serve as the pre-treatment for amorphization by pulverization of the substrate. From such viewpoint, the pulverization apparatus used in the present invention is preferably a tumbling ball mill, a vibrating ball mill, a mixing mill or a planetary ball mill, which is used for the pre-treatment for amorphization of cellulose, more preferably a pot mill classified as the tumbling ball mill, a media agitating mill classified as the mixing mill, or the planetary ball mill. It should be noted that a study made by the inventors of the present invention to be mentioned later suggests that reactivity tends to increase when a raw material obtained by a simultaneous pulverization treatment for a solid catalyst and a solid substrate has a high bulk density. Therefore, it is more preferred to use the tumbling ball mill, the mixing mill or the planetary ball mill that can apply a strong compression force enough to allow a pulverized product of the solid catalyst to dig into a pulverized product of the solid substrate.

A ratio between the solid catalyst and the solid substrate to be treated is not particularly limited, but from the viewpoints of hydrolysis efficiency in a reaction, a decrease in a substrate residue after the reaction, and a recovery rate of a produced sugar, a mass ratio between the solid catalyst and the solid substrate is preferably 1:100 to 10:1, more preferably 1:10 to 1:1.

In the raw materials after the treatment, the substrate and catalyst may be homogeneously and finely pulverized, and the average particle size after the fine pulverization (median diameter: particle size at a point where the cumulative volume curve determined based on the total powder volume defined as 100% crosses 50%) is 1 to 100 μm, preferably 1 to 30 μm, more preferably 1 to 20 μm from the viewpoint of improving reactivity. When the particle size of a raw material to be treated is large, in order to efficiently perform the fine pulverization, an appropriate pulverization treatment may be performed before the fine pulverization with, for example: a coarse crusher such as a shredder, a jaw crusher, a gyratory crusher, a cone crusher, a hammer crusher, a roll crusher, or a roll mill; or a medium crusher such as a stamp mill, an edge runner, a cutting/shearing mill, a rod mill, an autogenous mill, or a roller mill. The time for treating the raw material is not particularly limited as long as the raw material can be homogeneously and finely pulverized by the treatment.

[Hydrolysis Reaction]

Hydrolysis using a polysaccharide derived from a plant biomass as a substrate is carried out in the presence of a catalyst and water by heating the substrate preferably at a temperature to achieve a pressurized state. For example, the temperature to achieve the pressurized state is suitably set within a range of 110 to 380° C. From the viewpoints of performing rapid hydrolysis of cellulose and suppressing conversion of glucose obtained as a product into another sugar, the temperature is preferably a relatively high temperature, and is suitably set within a range of, for example, 170 to 320° C., more preferably 200 to 300° C., still more preferably 210 to 260° C., most preferably 215 to 250° C.

Hydrolysis of cellulose in the saccharification method of the present invention is usually carried out in a closed vessel such as an autoclave. Therefore, even if the pressure at the start of the reaction is ordinary pressure, the reaction system becomes a pressurized state when heated at the above-mentioned temperature. Further, the closed vessel may be pressurized before the reaction or during the reaction to perform the reaction. The pressure for pressurization is, for example, 0.1 to 30 MPa, preferably 1 to 20 MPa, more preferably 2 to 10 MPa. In addition to the closed vessel, the reaction solution may be heated and pressurized to perform the reaction while the reaction solution is allowed to flow by a high-pressure pump.

The amount of water for hydrolysis is at least one necessary for hydrolysis of the total amount of cellulose. In consideration of, for example, fluidity and stirring property of the reaction mixture, a mass ratio between water and cellulose may be controlled within a range of 1 to 500, preferably 2 to 200.

The atmosphere of the hydrolysis is not particularly limited. From an industrial viewpoint, the hydrolysis is preferably carried out under an air atmosphere, or may be carried out under an atmosphere of gas other than air, such as oxygen, nitrogen or hydrogen, or a mixture thereof.

From the viewpoint of increasing the yield of glucose, the heating for hydrolysis is preferably completed at the point when the rate of conversion of cellulose by hydrolysis falls within a range of 10 to 100% and the selectivity of glucose falls within a range of 20 to 80%. The point when the rate of conversion of cellulose by hydrolysis falls within a range of 10 to 100% and the selectivity of glucose falls within a range of 20 to 80% varies depending on the heating temperature, the type and amount of the catalyst to be used, the amount of water (ratio relative to cellulose), the type of cellulose, the stirring method and conditions, and the like. Therefore, the point may be determined based on an experiment after determination of the conditions. The heating time under usual conditions falls within, for example, a range of 5 to 60 minutes, preferably 5 to 30 minutes after the start of the heating for the hydrolysis reaction, but the time is not limited to the range. In addition, the heating for hydrolysis is suitably completed at the point when the rate of conversion of cellulose by hydrolysis falls within a range of preferably 30 to 100%, more preferably 40 to 100%, still more preferably 50 to 100%, most preferably 55 to 100% and the selectivity of glucose falls within a range of preferably 25 to 80%, more preferably 30 to 80%, most preferably 40 to 80%.

The hydrolysis reaction may be carried out in a batch fashion or a continuous fashion. The reaction is preferably carried out while stirring the reaction mixture.

In the present invention, it is possible to produce a sugar-containing solution that contains glucose as a major component and has a reduced amount of an excessive degradation product such as 5-hydroxymethylfurfural by performing a hydrolysis reaction at a relatively high temperature for a relatively short time.

After completion of heating, the reaction solution is preferably cooled from the viewpoint of suppressing conversion of glucose into another sugar to increase the yield of glucose. From the viewpoint of increasing the yield of glucose, the cooling of the reaction solution is carried out under conditions where the selectivity of glucose is maintained in a range of preferably 20 to 80%, more preferably 25 to 80%, still more preferably 30 to 80%, most preferably 40 to 80%.

From the viewpoint of increasing the yield of glucose, the cooling of the reaction solution is preferably carried out as fast as possible to a temperature at which conversion of glucose into another sugar is not substantially caused. For example, the cooling may be carried out at a speed in a range of 1 to 200° C./min and is preferably carried out at a speed in a range of 10 to 150° C./min. The temperature at which conversion of glucose into another sugar is not substantially caused is, for example, 150° C. or less, preferably 110° C. or less. That is, the reaction solution is suitably cooled to 150° C. or less at a speed in a range of 1 to 200° C./min, preferably 10 to 150° C./min, more suitably cooled to 110° C. or less at a speed in a range of 1 to 200° C./min, preferably 10 to 150° C./min.

EXAMPLES

Hereinafter, the present invention is described in more details byway of Examples and Comparative Examples. However, the present invention is by no means limited to the descriptions of Examples and Comparative Examples.

Measurement methods for median diameters and bulk densities of hydrolysis reaction raw materials used in Examples and Comparative Examples, and a hydrolysis method for the raw materials are as follows.

[Median Diameter]

A sample was dispersed in water and measured for its median diameter with a laser diffraction particle size distribution analyzer (manufactured by Nikkiso Co., Ltd., Microtrac MT3300EXII).

[Bulk Density]

The bulk density was determined by: gently placing 2 g of a sample in a dried 10-mL graduated cylinder (minimum scale: 0.1 mL) so that the surface of the powder was flat without compaction, measuring the volume of the sample, and dividing the mass by the volume.

[Solid Substrate]

In Examples and Comparative Examples, Avicel (microcrystalline cellulose manufactured by Merck Co.) was used as a reagent-grade solid substrate, and a polysaccharide derived from a plant biomass obtained by purifying bagasse by the following method (hereinafter referred to as purified bagasse) was used as an actual-biomass-grade solid substrate.

[Bagasse Purification Treatment Method]

To a high-pressure reactor (internal volume: 100 mL, autoclave manufactured by Nitto Koatsu Co., made of SUS316) were added 4.5 g of dried bagasse roughly pulverized with a rotary speed mill (manufactured by Fritsch Japan Co., Ltd., ring sieve: 0.12 mm) and 50 mL of water, and the reaction solution was heated at a temperature of 200° C. for 9 minutes while being stirred at 600 rpm, cooled, and treated with a centrifugal filter (manufactured by Kokusan Co., Ltd., H-110A) to collect 10.5 g of solid content (water content: 70%).

Subsequently, 10.5 g of the collected solid content were placed in the high-pressure reactor (internal volume: 100 mL, autoclave manufactured by Nitto Koatsu Co., made of SUS316) again together with 0.61 g of NaOH, 0.20 g of $Na_2S$ and 40 mL of water, and the resultant reaction solution was heated at a temperature of 160° C. for 60 minutes while being stirred at 600 rpm, cooled, and subjected to solid-liquid separation using the centrifugal filter (manufactured by Kokusan Co., Ltd., H-110A). The supernatant was removed, and 105 g of water were supplied to the centrifugal filter to wash the residue. Then, 6.0 g of the collected solid content (water content: 70%) were dried in an oven at 80° C. for 24 hours, thereby obtaining purified bagasse (1.8 g, cellulose content: 88%, hemicellulose content: 10%).

The cellulose content and hemicellulose content of the solid substrate were determined by analysis methods (Technical Report NREL/TP-510-42618) of NREL (the National Renewable Energy Laboratory).

[Hydrolysis Reaction]

The cellulose hydrolysis reaction was carried out by adding any mass ranging from 0.374 g (Avicel: 2.0 mmol, purified bagasse: 1.8 mmol, based on $C_6H_{10}O_5$ unit) to 14.960 g (Avicel: 80.0 mmol, purified bagasse: 70.4 mmol, based on $C_6H_{10}O_5$ unit) of simultaneously pulverized raw materials or mixed raw materials prepared in Examples or Comparative examples to be mentioned later and 40 mL of water to a high-pressure reactor (internal volume: 100 mL, autoclave manufactured by Nitto Koatsu Co., made of SUS316), and heating the mixture from room temperature to 230° C. in about 20 minutes while stirring the mixture at 600 rpm. Heating was stopped as soon as the temperature reached 230° C., and the reactor was cooled in a water bath. After cooling, the reaction solution was separated into a liquid and a solid by a centrifuge. The products in the liquid phase were quantitatively analyzed with a high-performance liquid chromatograph (apparatus: Shodex high-performance liquid chromatography manufactured by Showa Denko K.K., column: Shodex (registered trademark) 1KS801, mobile phase: water at 0.6 mL/min, 75° C., detection: differential refractive index). In addition, the solid residue was washed with water and dried at 110° C. for 24 hours, and a rate of conversion of cellulose was determined based on a mass of unreacted cellulose.

Equations for calculating the yield, rate of conversion of cellulose, and selectivity of glucose are shown below.

Yield of soluble component (%)={(molar number of carbon in component of interest)/(molar number of carbon in added cellulose)}×100 [Math. 1]

Rate of conversion of cellulose (%)=[1−(mass of recovered cellulose)/(mass of added cellulose)]×100 [Math. 2]

Selectivity of glucose (%)={(yield of glucose)/(rate of conversion of cellulose)}×100 [Math. 3]

Yield of unknown product (%)=rate of conversion of cellulose−total yield of soluble components [Math. 4]

Concentration of conversion of cellulose (%)=rate of conversion of cellulose×concentration of substrate×100 [Math. 5]

Example 1

Hydrolysis Reaction of Simultaneously Pulverized Avicel

An alkali-activated porous carbon material having a particle diameter of 1 μm or more and 30 μm or less (SDK-261, median diameter: 13 μm (manufactured by Showa Denko K. K.)) was obtained by activating coke by a heat treatment at 700° C., fine pulverization using a jet mill, addition of potassium hydroxide, and another heat treatment at 700° C.; and subsequent washing with water, neutralization with hydrochloric acid, boiling with hot water, drying and sieving. 3.00 g of Avicel (microcrystalline cellulose manufactured by Merck Co.) as a substrate and 0.46 g of the alkali-activated porous carbon material as a catalyst (mass ratio between the substrate and the catalyst: 6.5:1.0) were placed in a 500 mL-volume ceramic pot mill together with 300 g of zirconia balls each having a diameter of 1.5 cm. The ceramic pot mill was set to a desktop pot mill rotating table (manufactured by IRIE SHOKAI Co., Ltd., desktop pot mill type V-1M), and the mixture was subjected to a ball mill treatment at 60 rpm for 48 hours. The hydrolysis reaction was carried out using 0.374 g of the resultant simultaneously pulverized raw material including the substrate and the catalyst.

Example 2

The hydrolysis reaction was carried out using 3.740 g (10-fold weight of 0.374 g) of a simultaneously pulverized raw material obtained by performing the simultaneous pulverization step in Example 1 in a plurality of batches.

Example 3

The hydrolysis reaction was carried out using 7.480 g (20-fold weight of 0.374 g) of a simultaneously pulverized raw material obtained by performing the simultaneous pulverization step in Example 1 in a plurality of batches.

Example 4

The hydrolysis reaction was carried out using 11.220 g (30-fold weight of 0.374 g) of a simultaneously pulverized raw material obtained by performing the simultaneous pulverization step in Example 1 in a plurality of batches.

Example 5

The hydrolysis reaction was carried out using 14.960 g (40-fold weight of 0.374 g) of a simultaneously pulverized raw material obtained by performing the simultaneous pulverization step in Example 1 in a plurality of batches.

Comparative Example 1

Avicel (microcrystalline cellulose manufactured by Merck Co.) as a substrate and the alkali-activated porous carbon material used in Example 1 (SDK-261, median diameter: 13 μm) as a catalyst were used without pulverization to prepare a mixed raw material having a mass ratio between the substrate and the catalyst of 6.5:1.0. The hydrolysis reaction was carried out using the mixed raw material.

Comparative Examples 2 to 5

A separate pulverization treatment for a substrate and a catalyst was carried out as follows. 3.00 g of Avicel (microcrystalline cellulose manufactured by Merck Co.) as the substrate and 3.0 g of the alkali-activated porous carbon material used in Example 1 (SDK-261, median diameter: 13 μm) as the catalyst were separately placed in a 500 mL-volume ceramic pot mill together with 300 g of zirconia balls each having a diameter of 1.5 cm. The ceramic pot mill was set to a desktop pot mill rotating table (manufactured by IRIE SHOKAI Co., Ltd., desktop pot mill type V-1M), and the mixture was subjected to a ball mill treatment at 60 rpm for 48 hours. The resultant pulverized substrate and pulverized catalyst were used in combination with the unpulverized catalyst to prepare a mixed raw material of the pulverized substrate and the unpulverized catalyst (Comparative Example 2) and a mixed raw material of the pulverized substrate and the pulverized catalyst (Comparative Examples 3 to 5), each having a mass ratio between the substrate and the catalyst of 6.5:1.0. The hydrolysis reaction was carried out in the same way as in Example 1 using the mixed raw materials. It should be noted that, in Comparative Examples 3 to 5, the raw material was fed in different amounts to the reaction solution. The amount of the raw material in Comparative Example 4 was 10 times larger than that in Comparative Example 3, and the amount of the raw material in Comparative Example 5 was 30 times larger than that in Comparative Example 3.

Example 6

3.00 g of the purified bagasse as a substrate and 0.46 g of the alkali-activated porous carbon material used in Example 1 (SDK-261, median diameter: 13 μm) as a catalyst (mass ratio between the substrate and the catalyst: 6.5:1.0) were placed in a 500 mL-volume ceramic pot mill together with 300 g of zirconia balls each having a diameter of 1.5 cm. The ceramic pot mill was set to a desktop pot mill rotating table (manufactured by IRIE SHOKAI Co., Ltd., desktop pot mill type V-1M), and the mixture was subjected to a ball mill treatment at 60 rpm for 48 hours. The hydrolysis reaction was carried out using 0.374 g of the resultant simultaneously pulverized raw material including the substrate and the catalyst.

Example 7

The hydrolysis reaction was carried out using 11.220 g (30-fold weight of 0.374 g) of the simultaneously pulverized raw material prepared in Example 6.

Comparative Example 6

The purified bagasse as a substrate and the alkali-activated porous carbon material used in Example 1 (SDK-261, median diameter: 13 μm) as a catalyst were used without pulverization to prepare a mixed raw material having a mass ratio between the substrate and the catalyst of 6.5:1.0. The hydrolysis reaction was carried out using the mixed raw material.

Comparative Examples 7 and 8

A separate pulverization treatment for a substrate and a catalyst was carried out as follows. 3.00 g of the purified bagasse as the substrate and 3.0 g of the alkali-activated porous carbon material used in Example 1 (SDK-261, median diameter: 13 μm) as the catalyst were separately placed in a 500 mL-volume ceramic pot mill together with 300 g of zirconia balls each having a diameter of 1.5 cm. The ceramic pot mill was set to a desktop pot mill rotating table (manufactured by IRIE SHOKAI Co., Ltd., desktop pot mill type V-1M), and the mixture was subjected to a ball mill treatment at 60 rpm for 48 hours. The resultant pulverized substrate and pulverized catalyst were used in combination with the unpulverized catalyst to prepare a mixed raw material of the pulverized substrate and the unpulverized catalyst (Comparative Example 7) and a mixed raw material of the pulverized substrate and the pulverized catalyst (Comparative Example 8), each having a mass ratio between the substrate and the catalyst of 6.5:1.0. The hydrolysis reaction was carried out in the same way as in Example 1 using the mixed raw materials.

Table 1 collectively shows the results of measurement of median diameters and bulk densities of the following raw materials:
the unpulverized substrate (Avicel),
the unpulverized catalyst,
the separately pulverized substrate (Avicel),
the separately pulverized catalyst,
the mixed raw material of the unpulverized substrate (Avicel) and the unpulverized catalyst (Comparative Example 1),
the mixed raw material of the separately pulverized substrate (Avicel) and the unpulverized catalyst (Comparative Example 2),
the mixed raw material of the separately pulverized substrate (Avicel) and the separately pulverized catalyst (Comparative Examples 3 to 5),
the simultaneously pulverized raw material of the substrate (Avicel) and the catalyst (Examples 1 to 5),
the unpulverized substrate (purified bagasse), the separately pulverized substrate (purified bagasse),
the mixed raw material of the unpulverized substrate (purified bagasse) and the unpulverized catalyst (Comparative Example 6), the mixed raw material of the separately pulverized substrate (purified bagasse) and the unpulverized catalyst (Comparative Example 7),
the mixed raw material of the separately pulverized substrate (purified bagasse) and the separately pulverized catalyst (Comparative Example 8), and
the simultaneously pulverized raw material of the substrate (purified bagasse) and the catalyst (Examples 6 and 7).

The pulverization decreased the median diameters and increased the bulk densities, which confirmed that the pulverization decreased the particle sizes and increased the densities of the particles. Comparisons between the separately pulverized mixed raw material of each of Comparative Examples 3 to 5 and the simultaneously pulverized raw material of each of Examples 1 to 5, and between the separately pulverized mixed raw material of Comparative Example 8 and the simultaneously pulverized raw material of each of Examples 6 and 7, each having a substrate-catalyst mass ratio of 6.5:1.0, each confirmed the following fact. The separately pulverized mixed raw material and the simultaneously pulverized raw material had the same average particle size, while the simultaneously pulverized raw material had a bulk density larger than that of the separately pulverized mixed raw material and was present at a higher density.

TABLE 1

| Sample | Median diameter (μm) | Bulk density (g/mL) |
|---|---|---|
| Unpulverized substrate (Avicel) | 30 | 0.48 |
| Pulverized substrate (Avicel) | 17 | 0.53 |
| Unpulverized catalyst | 13 | 0.22 |
| Pulverized catalyst | 2 | 0.24 |
| Mixed product of Unpulverized substrate (Avicel) and unpulverized catalyst having mass ratio of 6.5:1.0 (Comparative Example 1) | 28 | 0.41 |
| Mixed product of pulverized substrate (Avicel) and unpulverized catalyst having mass ratio of 6.5:1.0 (Comparative Example 2) | 16 | 0.44 |
| Mixed product of pulverized substrate (Avicel) and pulverized catalyst having mass ratio of 6.5:1.0 (Comparative Examples 3 to 5) | 15 | 0.45 |
| Simultaneously pulverized mixed product of unpulverized substrate (Avicel) and unpulverized catalyst having mass ratio of 6.5:1.0 (Examples 1 to 5) | 15 | 0.47 |
| Unpulverized substrate (purified bagasse) | 100 | 0.43 |
| Pulverized substrate (purified bagasse) | 18 | 0.52 |
| Mixed product of unpulverized substrate (purified bagasse) and unpulverized catalyst having mass ratio of 6.5:1.0 (Comparative Example 6) | 95 | 0.42 |
| Mixed product of pulverized substrate (purified bagasse) and unpulverized catalyst having mass ratio of 6.5:1.0 (Comparative Example 7) | 17 | 0.44 |
| Mixed product of pulverized substrate (purified bagasse) and pulverized catalyst having mass ratio of 6.5:1.0 (Comparative Example 8) | 16 | 0.45 |
| Simultaneously pulverized mixed product of unpulverized substrate (purified bagasse) and unpulverized catalyst having mass ratio of 6.5:1.0 (Examples 6 and 7) | 16 | 0.47 |

Figure 2:
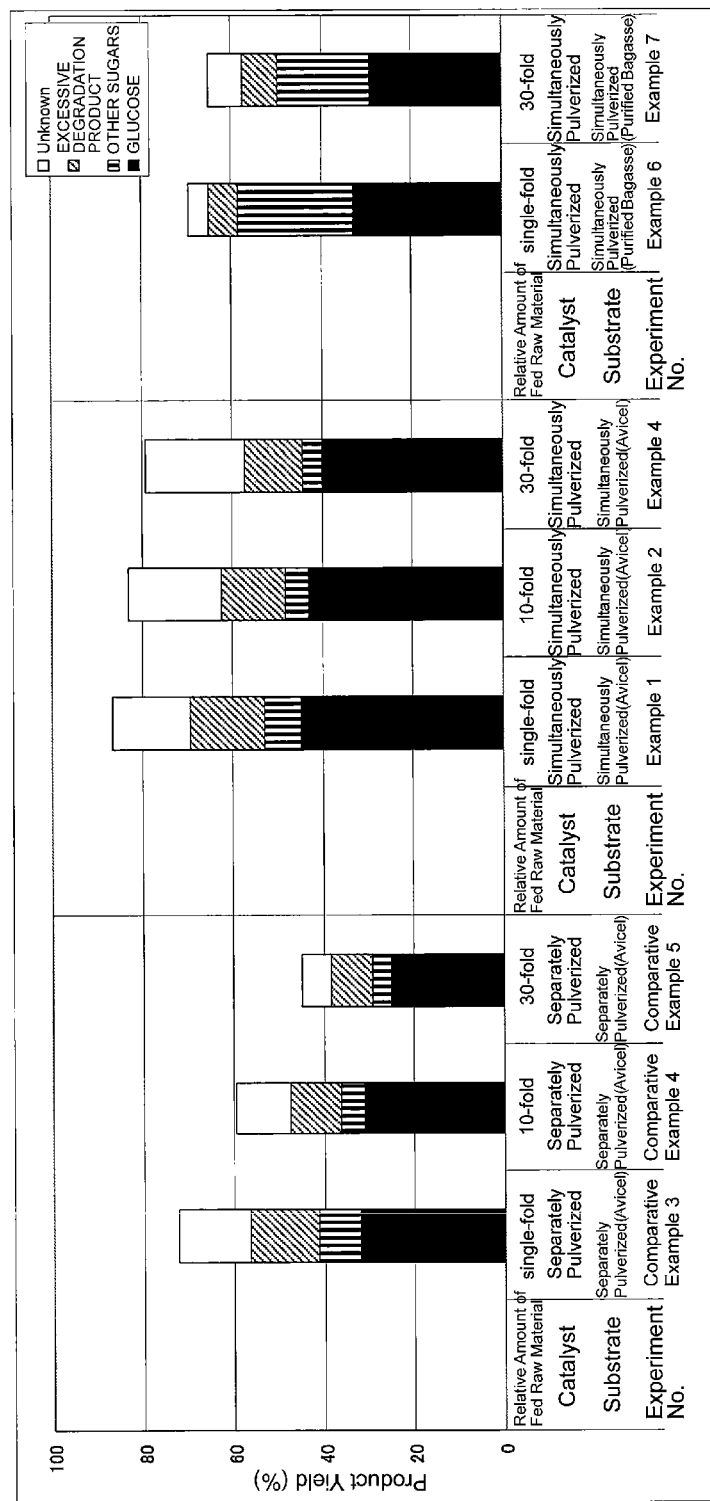
FIG. 2 is a graph showing relationships between amounts of fed raw materials and product yields under different pulverization conditions (separately pulverized and mixed or simultaneously pulverized) of a substrate (Avicel or purified bagasse) and a catalyst as a reaction raw material. In the figure, the black part represents a yield of glucose, the vertical stripe part represents a yield of a sugar other than glucose, the shaded part represents a yield of an excessive degradation product, and the white part represents a yield of an unknown substance.
Figure 3:
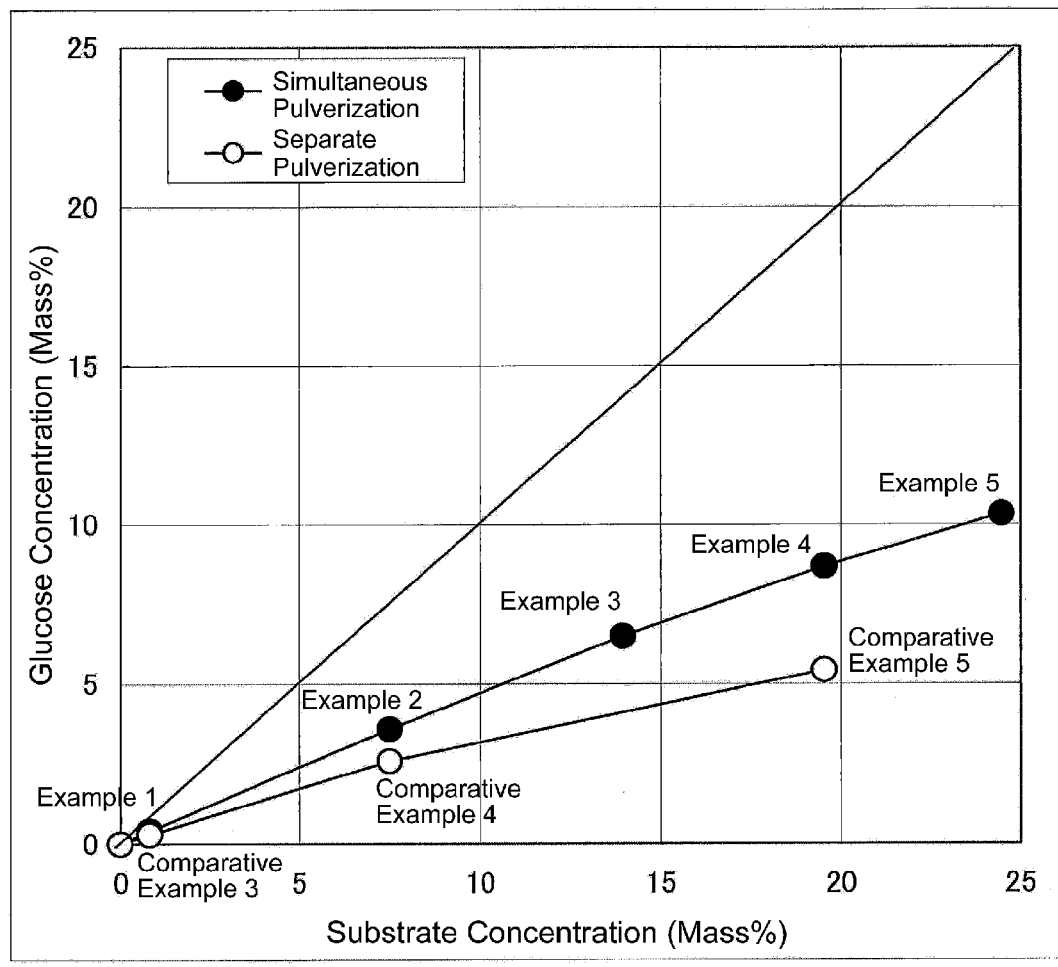
FIG. 3 is a graph showing correlations between substrate concentrations in reaction solutions and glucose concentrations in products under different pulverization conditions (separately pulverized and mixed or simultaneously pulverized) of a substrate (Avicel) and a catalyst as a reaction raw material.
Figure 4:
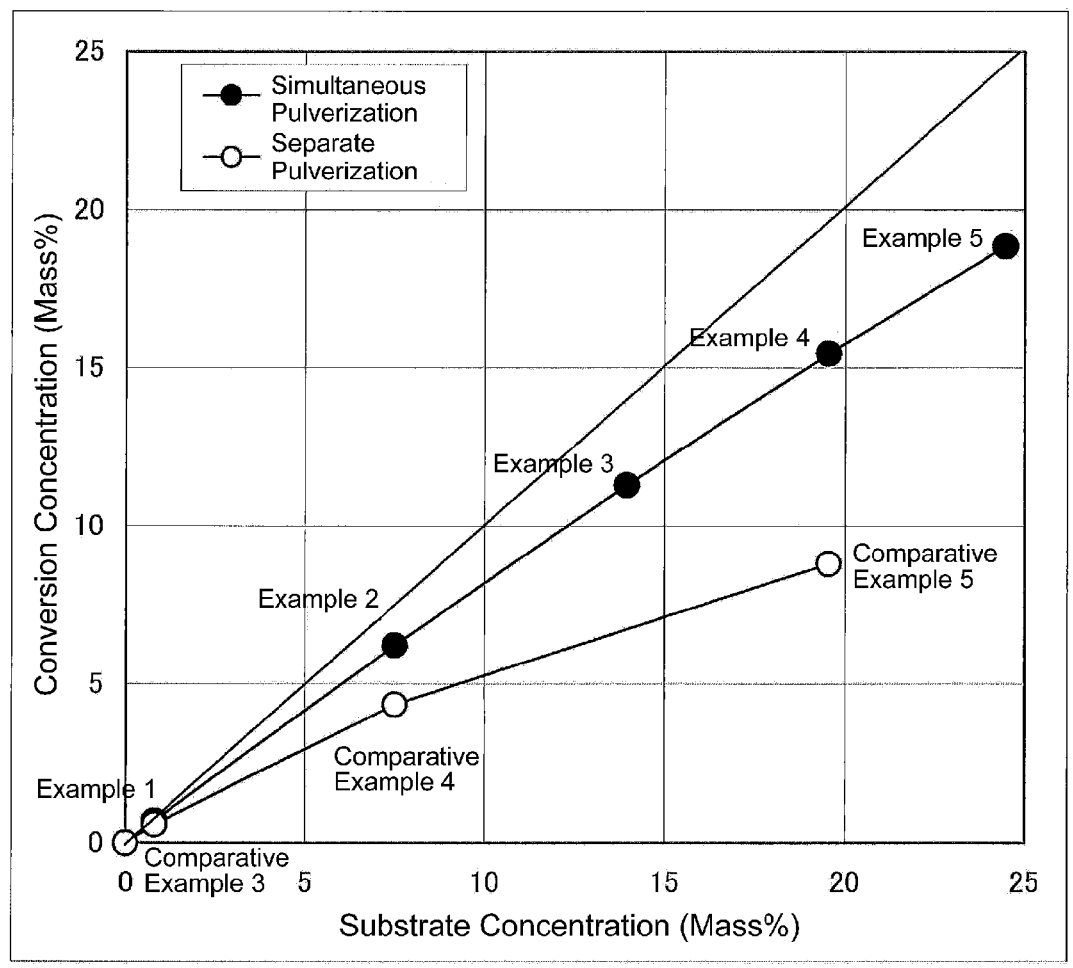
FIG. 4 is a graph showing correlations between substrate concentrations in reaction solutions and rates of conversion under different pulverization conditions (separately pulverized and mixed or simultaneously pulverized) of a substrate (Avicel) and a catalyst as a reaction raw material.

Table 2 collectively shows the results of the hydrolysis reactions in Examples 1 to 7 and Comparative Examples 1 to 8. In addition, FIG. 1 shows relationships between pulverization conditions of the substrates and catalyst used as reaction raw materials and product yields, FIG. 2 shows relationships between raw material feed amounts and product yields under different pulverization conditions (separate pulverization and mixing, and simultaneous pulverization) of the substrates and catalyst used as reaction raw materials, and FIGS. 3 and 4 show correlations of concentrations of the substrate (Avicel) in reaction solutions with concentrations of glucose in products and conversion rates, respectively, under different pulverization conditions (separate pulverization and mixing, and simultaneous pulverization) of the substrate (Avicel) and catalyst used as reaction raw materials.

TABLE 2

| | | Conditions | | | Results Product concentration (%) | |
|---|---|---|---|---|---|---|
| | Raw material pulverization | Raw material feed amount (g) a) | Relative amount of fed raw material b) | Substrate concentration (%) c) | Glucose d) | Conversion concentration |
| Example 1 | Simultaneous pulverization (Avicel + catalyst) | 0.375 | Single-fold | 0.80 | 0.40 | 0.70 |
| Example 2 | Simultaneous pulverization (Avicel + catalyst) | 3.750 | 10-fold | 7.49 | 3.58 | 6.22 |
| Example 3 | Simultaneous pulverization (Avicel + catalyst) | 7.480 | 20-fold | 13.94 | 6.51 | 11.29 |
| Example 4 | Simultaneous pulverization (Avicel + catalyst) | 11.220 | 30-fold | 19.55 | 8.69 | 15.44 |
| Example 5 | Simultaneous pulverization (Avicel + catalyst) | 14.960 | 40-fold | 24.47 | 10.33 | 18.84 |
| Comparative Example 1 | Unpulverized substrate (Avicel) and catalyst | 0.375 | Single-fold | 0.80 | 0.10 | 0.22 |
| Comparative Example 2 | Separate pulverization of substrate (Avicel) alone | 0.375 | Single-fold | 0.80 | 0.24 | 0.47 |
| Comparative Example 3 | Separate pulverization of substrate (Avicel) and catalyst | 0.375 | Single-fold | 0.80 | 0.29 | 0.58 |
| Comparative Example 4 | Separate pulverization of substrate (Avicel) and catalyst | 3.750 | 10-fold | 7.49 | 2.58 | 4.35 |
| Comparative Example 5 | Separate pulverization of substrate (Avicel) and catalyst | 11.220 | 30-fold | 19.55 | 5.43 | 8.80 |
| Example 6 | Simultaneous pulverization (purified bagasse + catalyst) | 0.375 | Single-fold | 0.70 | 0.26 | 0.49 |
| Example 7 | Simultaneous pulverization (purified bagasse + catalyst) | 11.220 | 30-fold | 17.20 | 5.61 | 11.19 |
| Comparative Example 6 | Unpulverized substrate (purified bagasse) and catalyst | 0.375 | Single-fold | 0.70 | 0.01 | 0.02 |
| Comparative Example 7 | Separate pulverization of substrate (purified bagasse) alone | 0.375 | Single-fold | 0.70 | 0.15 | 0.28 |
| Comparative Example 8 | Separate pulverization of substrate (purified bagasse) and catalyst | 0.375 | Single-fold | 0.70 | 0.18 | 0.30 |

| | Results Product yield (%, relative to carbon) | | | | Cellulose conversion rate (%) | Glucose selectivity (%) |
|---|---|---|---|---|---|---|
| | Glucose | Other sugars e) | Excessive degradation product f) | unknown | | |
| Example 1 | 45.0 | 7.9 | 16.6 | 17.2 | 86.7 | 51.9 |
| Example 2 | 43.0 | 5.3 | 14.2 | 20.6 | 83.0 | 51.8 |
| Example 3 | 42.0 | 4.9 | 12.5 | 21.7 | 81.0 | 51.9 |
| Example 4 | 40.0 | 4.5 | 12.6 | 21.9 | 79.0 | 50.6 |
| Example 5 | 38.0 | 3.7 | 13.1 | 22.2 | 77.0 | 49.4 |
| Comparative Example 1 | 11.3 | 4.0 | 4.2 | 8.0 | 27.5 | 40.9 |
| Comparative Example 2 | 26.6 | 9.9 | 11.1 | 11.2 | 58.8 | 45.2 |
| Comparative Example 3 | 32.0 | 9.3 | 15.0 | 15.9 | 72.2 | 44.3 |
| Comparative Example 4 | 31.0 | 5.3 | 11.3 | 12.0 | 58.0 | 53.4 |
| Comparative Example 5 | 25.0 | 4.1 | 9.2 | 6.7 | 45.0 | 55.6 |
| Example 6 | 32.9 | 25.5 | 6.7 | 4.2 | 69.3 | 47.4 |
| Example 7 | 29.3 | 20.3 | 7.9 | 7.5 | 65.0 | 45.1 |
| Comparative Example 6 | 1.5 | 0.7 | 0.4 | 0.8 | 3.3 | 44.2 |

TABLE 2-continued

| | | | | | | |
|---|---|---|---|---|---|---|
| Comparative Example 7 | 18.7 | 9.3 | 0.3 | 10.7 | 39.1 | 47.9 |
| Comparative Example 8 | 23.0 | 12.8 | 2.4 | 4.9 | 43.2 | 53.3 | a) Total weight of fed substrate and catalyst
b) Relative to 0.375 g
c) Weight of fed substrate (g)/[weight of fed substrate (g) + 40 (g)] × 100
d) Glucose value measured by HPLC
e) Total of cellotetraose, cellotriose, cellobiose, mannose, and fructose
f) Total of levoglucosan, 5-hydroxymethylfurfural, and levoglucosan As shown in FIG. 1, the materials are arranged in order of increasing the glucose yields and conversion rates: i.e. no pulverization of the substrates and catalyst (Comparative Examples 1 and 6), separate pulverization of the substrates alone (Comparative Examples 2 and 7), separate pulverization of the substrates and catalyst (Comparative Examples 3 and 8), and simultaneous pulverization of the substrates and catalyst (Examples 1 and 6). Improvement of the yield of Comparative Example 1 to the yield of Comparative Example 2 (glucose yield: from 11.3% to 26.6%, conversion rate: from 27.5% to 58.8%) and improvement of the yield of Comparative Example 6 to the yield of Comparative Example 7 (glucose yield: from 1.5% to 18.7%, conversion rate: from 3.3% to 39.1%) were probably caused by pulverizing the substrates to lower crystallinity of the substrates, resulting in improving reactivity, while improvement of the yield of Comparative Example 2 to the yield of Comparative Example 3 (glucose yield: from 26.6% to 32.0%, conversion rate: from 58.8% to 72.2%) and improvement of the yield of Comparative Example 7 to the yield of Comparative Example 8 (glucose yield: from 18.7% to 23.0%, conversion rate: from 39.1% to 43.2%) were probably caused by pulverizing the catalyst to decrease the particle size, resulting in improving contact property with the substrates, and to expose an active site at which the effect in catalyst pores was not exhibited, resulting in providing an effective active point. It can be said that the results are ones that are presumed from findings based on the related art and reaction mechanisms.

On the other hand, although the raw materials of Comparative Example 3 and Example 1 had the same average particle size (15 μm), the simultaneous pulverization improved the glucose yield from 32.0% to 45.0% and the conversion rate from 72.2% to 86.7%. In addition, although the raw materials of Comparative Example 8 and Example 6 had the same average particle size (16 μm), the simultaneous pulverization improved the glucose yield from 23.0% to 32.9% and the conversion rate from 43.2% to 69.3%. The results confirmed that synergistic effects that greatly exceed a range estimated from conventional findings were provided. It is presumed that the synergistic effects were caused by any interaction capable of enhancing reactivity between the substrates and catalyst by the simultaneous treatment because the raw material of Example 1 prepared by simultaneous pulverization had a bulk density slightly larger than the raw materials prepared by separate pulverization.

It is presumed that the lower yields in the case of using the purified bagasse of actual biomass grade as the solid substrate (Example 6, Comparative Examples 6 to 8) compared with those in the case of using Avicel which is a reagent grade as the solid substrate (Example 1, Comparative Examples 1 to 3) were caused by differences in, for example, crystal structures of non-cellulose components such as lignin and hemicellulose and cellulose contained in the purified bagasse.

[Study on Increase in Concentration in Reaction]

The amount of the reaction raw material fed at a substrate concentration of 0.8% was defined as single-fold, and the same, 10-fold, and 30-fold amounts of the reaction raw material were fed. The results under the above-mentioned conditions (FIG. 2) are as follows. In the case of using Avicel as the substrate, the glucose yields in the case of separate pulverization were 32.0% (Comparative Example 3), 31.0% (Comparative Example 4), and 25.0% (Comparative Example 5), and the glucose yields in the case of simultaneous pulverization were 45.0% (Example 1), 43.0% (Example 2), and 40.0% (Example 4), while the conversion rates in the case of separate pulverization were 72.2%, 58.0%, and 45.0%, and the conversion rates in the case of simultaneous pulverization were 86.7%, 83.0%, and 79.0%.

In addition, in the case of simultaneous pulverization using the purified bagasse as the substrate, the glucose yields in the cases of the single-fold amount and the 30-fold amount were found to be 32.9% (Example 6) and 29.3% (Example 7), respectively, and the conversion rates were found to be 69.3% and 65.0%, respectively.

The respective values determined under the condition of the single-fold amount in the case of using Avicel as the substrate were defined as 100% and compared with the respective values determined under the condition of the 30-fold amount. As a result, the glucose yield in the case of separate pulverization and the glucose yield in the case of simultaneous pulverization were 78% and 89%, respectively, while the conversion rate in the case of separate pulverization and the conversion rate in the case of simultaneous pulverization were 62% and 91%, respectively.

The results confirmed that, in the case of simultaneous pulverization, decreases in the glucose yields and conversion rates due to the increase in the concentration were suppressed, and the values of the glucose yields and conversion rates were higher, as compared with separate pulverization.

The correlation graphs of the substrate concentrations of the reaction raw materials and the concentrations of glucose produced and conversion concentrations in the case of using Avicel as the substrate (FIGS. 3 and 4) show that the glucose concentrations under the condition of the 30-fold amount were 8.7 mass % in the case of simultaneous pulverization and 5.4 mass % in the case of separate pulverization, and the conversion concentrations were 15.4 mass % in the case of simultaneous pulverization and 8.8 mass % in the case of separate pulverization, which suggested that the concentrations in the case of simultaneous pulverization were significantly larger than those in the case of separate pulverization. Further, in the case of simultaneous pulverization, the decrease in the product yield due to the increase in the concentration tended to be smaller than that in the case of separate pulverization. In the case of simultaneous pulverization, the glucose concentration under the condition of the 40-fold amount was found to be 10.3 mass %.

INDUSTRIAL APPLICABILITY

The present invention is very useful for effective utilization of a biomass resource because the present invention can improve a reaction yield (saccharification yield) and a sugar concentration of a sugar containing a monosaccharide such as glucose as a major component in a reaction solution in a hydrolysis reaction of a plant biomass with a solid catalyst by hydrolyzing the catalyst and the substrate (plant biomass) after a simple treatment for preliminarily mixing and simultaneously pulverizing the catalyst and the substrate.

The invention claimed is:

1. A pre-treatment method for a plant biomass hydrolysis reaction raw material, comprising pulverization step that comprises simultaneously mixing and pulverizing a solid catalyst and a solid substrate,
   in which the solid catalyst is a carbon material which is alkali-activated carbon, steam-activated carbon, or mesoporous carbon and
   in which a median diameter of a mixture of the solid catalyst and the solid substrate as the reaction raw material after the pulverization step is 1 to 30 micrometer.

2. The pre-treatment method for a plant biomass hydrolysis reaction raw material according to claim 1, in which the solid substrate is a polysaccharide derived from a plant biomass.

3. The pre-treatment method for a plant biomass hydrolysis reaction raw material according to claim 1, in which the pulverization step is carried out using a tumbling ball mill, a vibrating ball mill, a mixing mill, or a planetary ball mill.

4. The pre-treatment method for a plant biomass hydrolysis reaction raw material according to claim 1, in which a mass ratio between the solid catalyst and the solid substrate is 1:100 to 10:1.

5. The pre-treatment method for a plant biomass hydrolysis reaction raw material according to claim 4, in which a mass ratio between the solid catalyst and the solid substrate is 1:10 to 1:1.

6. A plant biomass hydrolysis reaction raw material, which is treated by the pre-treatment method according to claim 1.

7. A saccharification method for a plant biomass, comprising the step of hydrolyzing the hydrolysis reaction raw material according to claim 6.

* * * * *